United States Patent [19]

Helmbreck

[11] 4,288,878
[45] Sep. 15, 1981

[54] PAINTER'S PROTECTIVE DEVICE

[75] Inventor: Andrew J. Helmbreck, Mesa, Ariz.

[73] Assignee: Russell C. Rogge, Scottsdale, Ariz.; a part interest

[21] Appl. No.: 14,786

[22] Filed: Feb. 23, 1979

[51] Int. Cl.³ .................................................. A61F 9/02
[52] U.S. Cl. ........................................... 2/427; 2/431; 2/433
[58] Field of Search ................... 2/433, 427, 426, 431, 2/439, 206, 12, 9

[56] References Cited

U.S. PATENT DOCUMENTS

| | | | |
|---|---|---|---|
| 854,546 | 5/1907 | Verdeau | 2/206 |
| 1,190,567 | 7/1916 | Malcom | 2/12 |
| 2,406,190 | 8/1946 | Burdick | 2/433 X |
| 2,655,657 | 10/1953 | Lueders | 2/12 |
| 3,530,506 | 9/1970 | Hoffmaster | 2/431 |

FOREIGN PATENT DOCUMENTS

| | | | |
|---|---|---|---|
| 580798 | 6/1933 | Fed. Rep. of Germany | 2/12 |
| 902775 | 12/1953 | Fed. Rep. of Germany | 2/12 |
| 684750 | 3/1930 | France | 2/433 |

Primary Examiner—Peter P. Nerbun
Attorney, Agent, or Firm—Charles E. Cates; Victor Myer

[57] ABSTRACT

The disclosure teaches a painter's protective device providing a mask adapted to cover the forehead, eyes and nose of the wearer and having suitable eye holes and a visor projecting outwardly from the forehead portion of the mask above the eye holes and means for retaining the mask on the wearer's head. In a preferred embodiment the eye holes are covered by a screen.

2 Claims, 7 Drawing Figures

PAINTER'S PROTECTIVE DEVICE

BACKGROUND OF THE INVENTION

This invention relates to devices for the protection of painters.

Painters using spray guns, especially of the airless type, suffer much inconvenience and even injury to the skin as a result of receiving deposits of paint on their faces and in their eyes which causes at the least redness and irritation.

The problem is particularly acute in overhead spraying from airless guns because the painter must look up to see what he is doing and certain amounts of the spray particles bounce off the surface to be painted and on to the face and into the eyes of the painter. To a somewhat lesser extent the same problem exists with air guns.

To applicant's knowledge, no person in the prior art has made a light-weight, inexpensive, satisfactory protective device in response to the problem. Accordingly, it is an object of this invention to respond to the problems heretofore described.

BRIEF SUMMARY OF THE INVENTION

In accordance with the invention more fully described hereafter there is provided a painter's protective device which has a mask adapted to cover the forehead, eyes and nose of the wearer, eye holes therein appropriately placed, a visor projecting outwardly from the forehead portion of the mask above the eye holes, and means for retaining the device on the wearer's head.

Conveniently, the eye holes may be narrow slits and the visor may be extended and curved downwardly at the ends to provide additional protection at the sides in the vicinity of the eye holes.

Preferably, the eye holes are covered by a screen material to give additional protection to the eyes.

BRIEF DESCRIPTION OF THE PREFERRED EMBODIMENT OF THE INVENTION

A fuller understanding of the invention may be obtained from the following drawings considered in connection with the detailed description that follows wherein.

Figure 1:
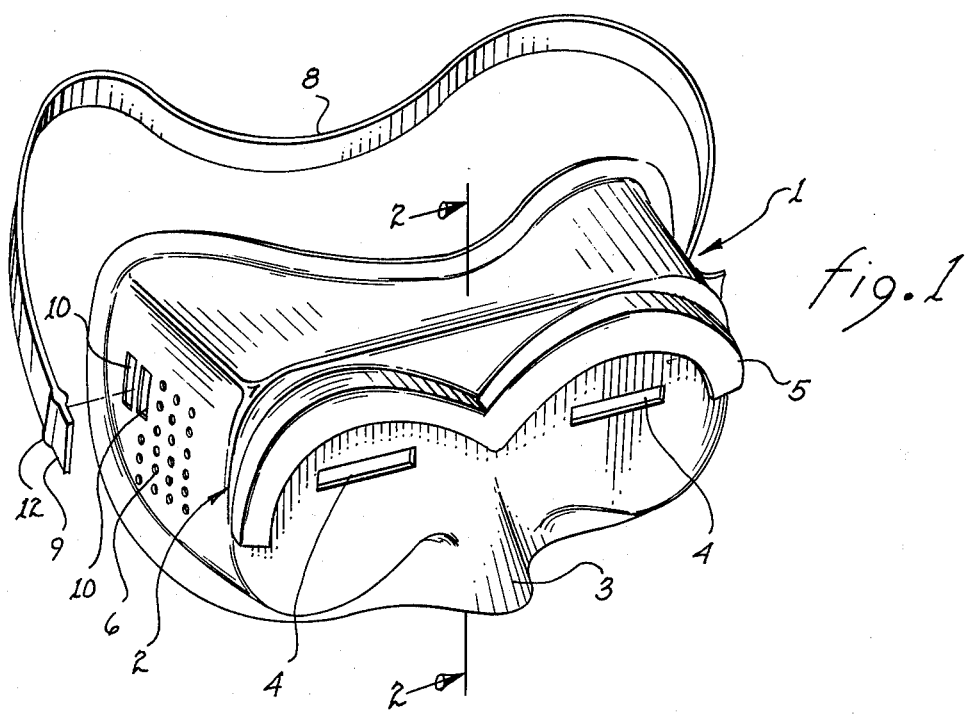
FIG. 1 is a perspective view of a presently preferred embodiment of the device.
Figure 2:
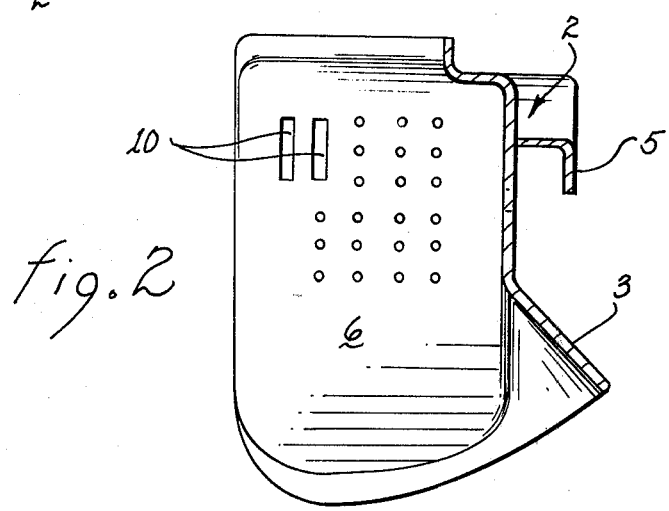
FIG. 2 is a side elevation view of the device of FIG. 1, taken in section along the lines 2—2.
Figure 3:
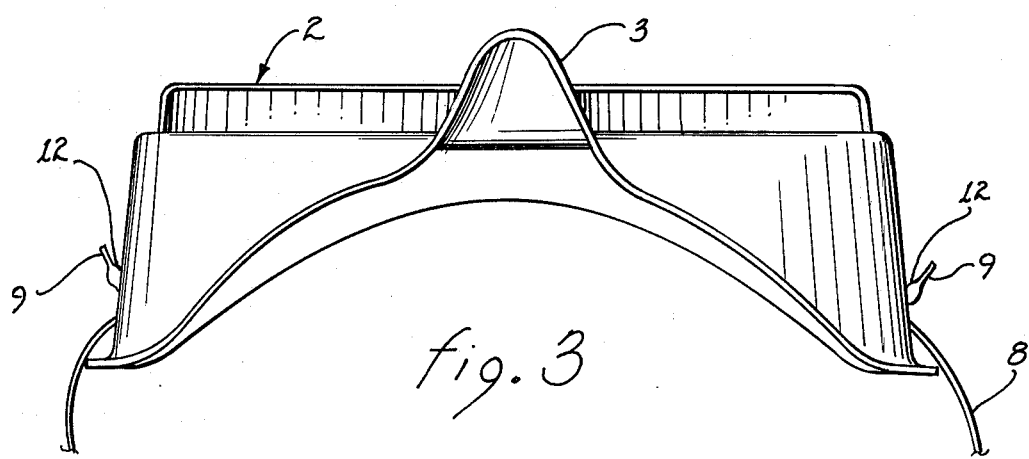
FIG. 3 is a bottom plan view of the device of FIG. 1, in section, along the lines 3—3.
Figure 4:
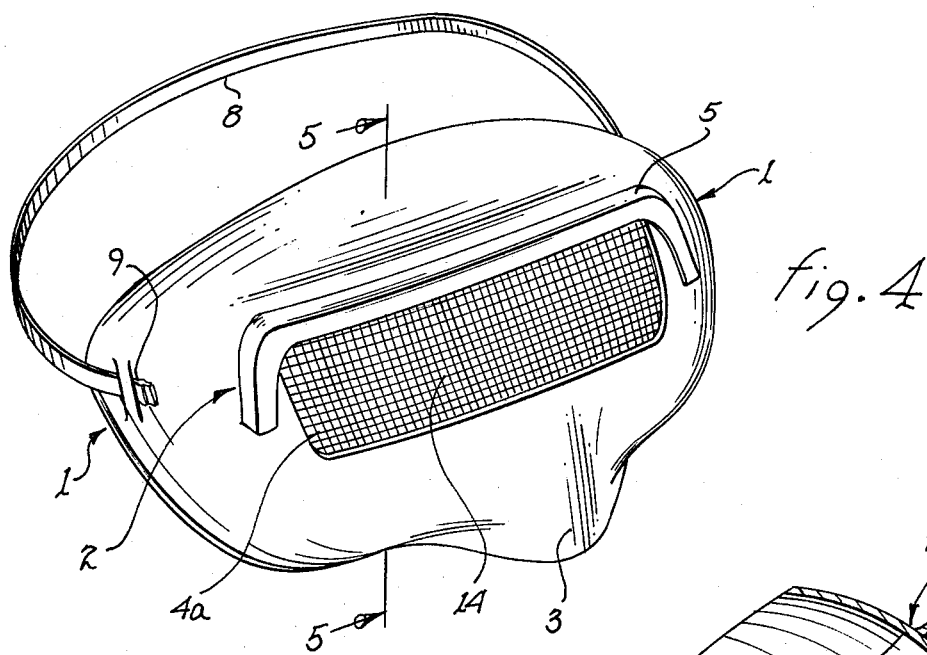
FIG. 4 is a perspective view of an alternative presently preferred embodiment of the device.
Figure 5:
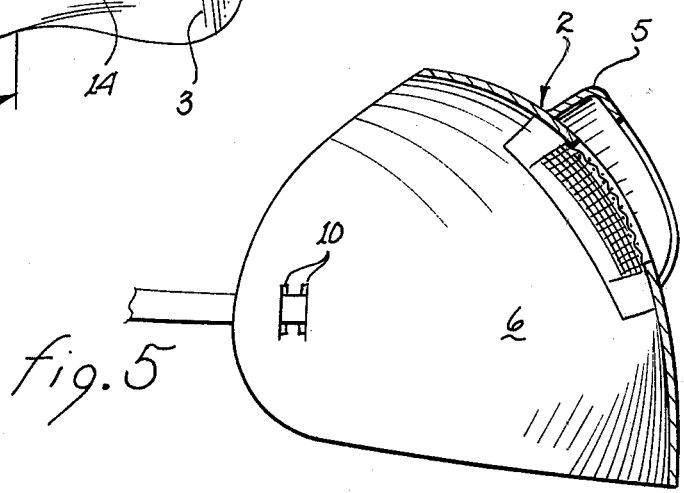
FIG. 5 is a view, in section, of the device of FIG. 4 taken along the lines 5—5.
Figure 6:
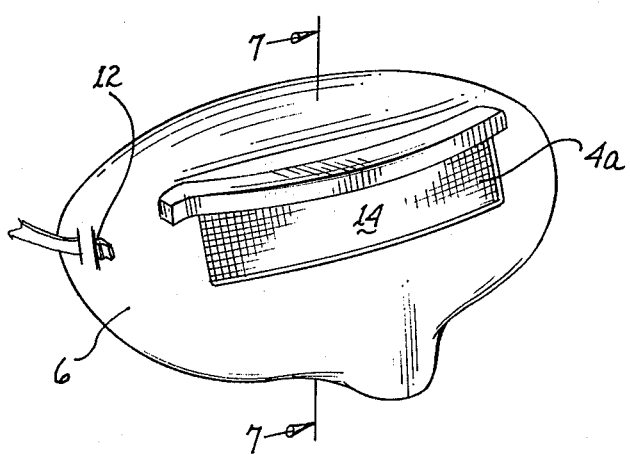
FIG. 6 is a perspective view of yet another preferred embodiment of the device.
Figure 7:
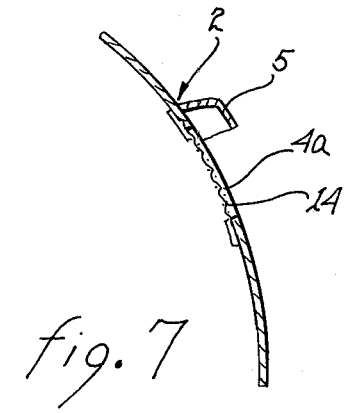
FIG. 7 is a view of the device of FIG. 6, in section, along the lines 7—7.

Referring now to the drawings wherein a presently preferred embodiment of the invention is depicted, with particular reference to FIGS. 1, 2 and 3 there is provided in the device a mask 1 which has a forehead area 2, a nose area 3 and eye holes 4. Projecting from the forehead area 2 is a visor 5 which has a horizontal component which is integrally formed into a downwardly and outwardly extending, vertically inclined, extension of the visor 5. The eye holes 4 in this embodiment are narrow, elongate strips. The mask is held in place on the head of the wearer by means of an elastic band 8 whose ends 9 are inserted through suitable apertures 10 in the sides 6 of the mask 1.

Referring now particularly to FIGS. 4–7 wherein the same parts are assigned the same numbers, the mask 1 is provided as an alternative embodiment with a large opening 4a covered by a screen 14.

Persons ordinarily skilled in the art will appreciate from a thoughtful consideration of the foregoing disclosure that various equivalents of the preferred embodiment may be employed.

All such embodiments as may be considered fairly to fall within the ambit of the appended claims are intended to be considered a part of this invention. /

What is claimed is:

1. A painter's protective device comprising a mask adapted to cover the forehead, eyes and nose of a wearer and having eye holes, a visor integral with said mask and projecting outwardly from the forehead portion of the mask above the eye holes and curving downwardly centrally and at the ends to the sides of the mask and said eye holes, and means for retaining said mask on the wearer's head.

2. The mask of claim 1 wherein said eye holes are narrow slits.

* * * * *